(12) United States Patent
Fleischer et al.

(10) Patent No.: US 6,439,047 B1
(45) Date of Patent: Aug. 27, 2002

(54) METHOD AND ARRANGEMENT FOR MECHANICALLY TESTING THE VALVE DISK OF CERAMIC VALVES

(75) Inventors: Holger Fleischer, Bad Liebenzell; Otto Iancu, Karlsruhe; Karl-Heinz Thiemann, Korb, all of (DE)

(73) Assignee: DaimlerChrysler AG, Stuttgart (DE)

( * ) Notice: Subject to any disclaimer, the term of this patent is extended or adjusted under 35 U.S.C. 154(b) by 0 days.

(21) Appl. No.: 09/417,129

(22) Filed: Oct. 13, 1999

(30) Foreign Application Priority Data

Oct. 13, 1999 (DE) .......................................... 198 47 210

(51) Int. Cl.⁷ ............................................. G01M 19/00
(52) U.S. Cl. ........................................................ 73/168
(58) Field of Search .......................... 73/168, 831, 774, 73/856, 857

(56) References Cited

U.S. PATENT DOCUMENTS 4,030,201 A * 6/1977 Posatti et al. ............. 33/174 Q
5,237,876 A * 8/1993 Liu .............................. 73/831
5,625,154 A * 4/1997 Matsuhiro et al. ............ 73/774

FOREIGN PATENT DOCUMENTS

| DE | 197 05 412 | 2/1997 |
| DE | 198 47 210 | 10/1998 |
| EP | 0660101 | 6/1995 |
| EP | 0660101 A2 | 6/1995 |
| FR | 2 784 463 | 10/1999 |
| JP | 3-264713 | 11/1991 |
| JP | 8 128935 | 5/1996 |
| JP | 2000131198 | 5/2000 |
| WO | WO98/36262 | 8/1998 |

* cited by examiner

Primary Examiner—Benjamin R. Fuller
Assistant Examiner—Octavia Davis
(74) Attorney, Agent, or Firm—Crowell & Moring LLP

(57) ABSTRACT

A method and an arrangement for testing valve disks of ceramic charge cycle valves for internal-combustion engines is provided. Two stressing rollers are pressed against a radially outer section of a valve seat side of the valve and a third stressing roller is provided against the other side of the valve intermediate the other two stressing rollers.

44 Claims, 4 Drawing Sheets

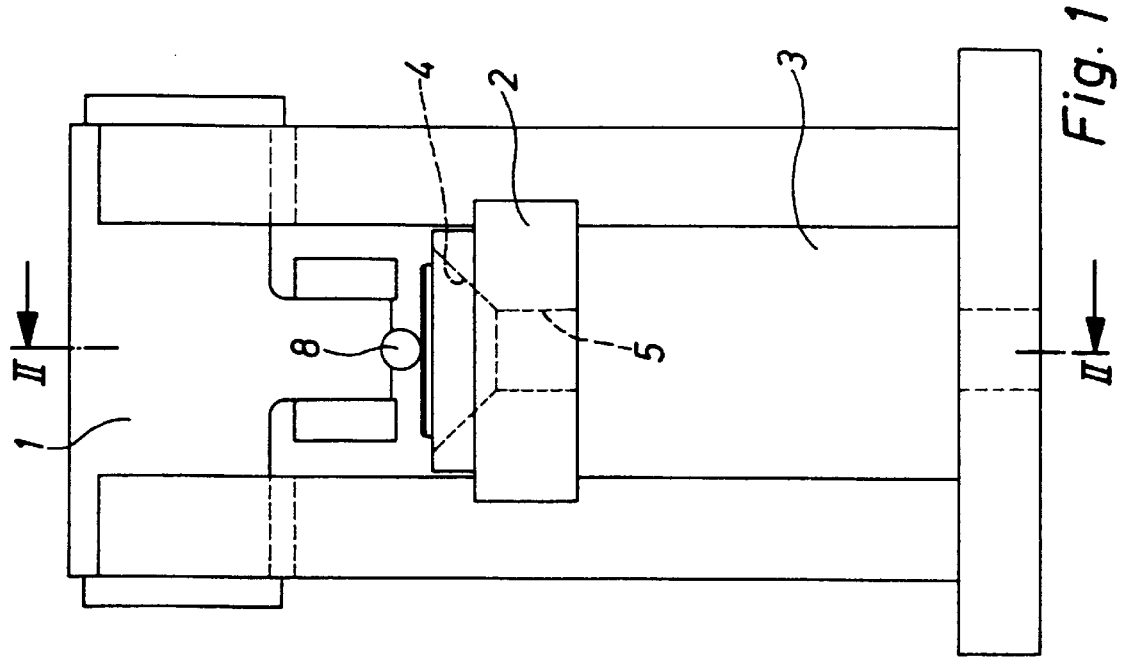
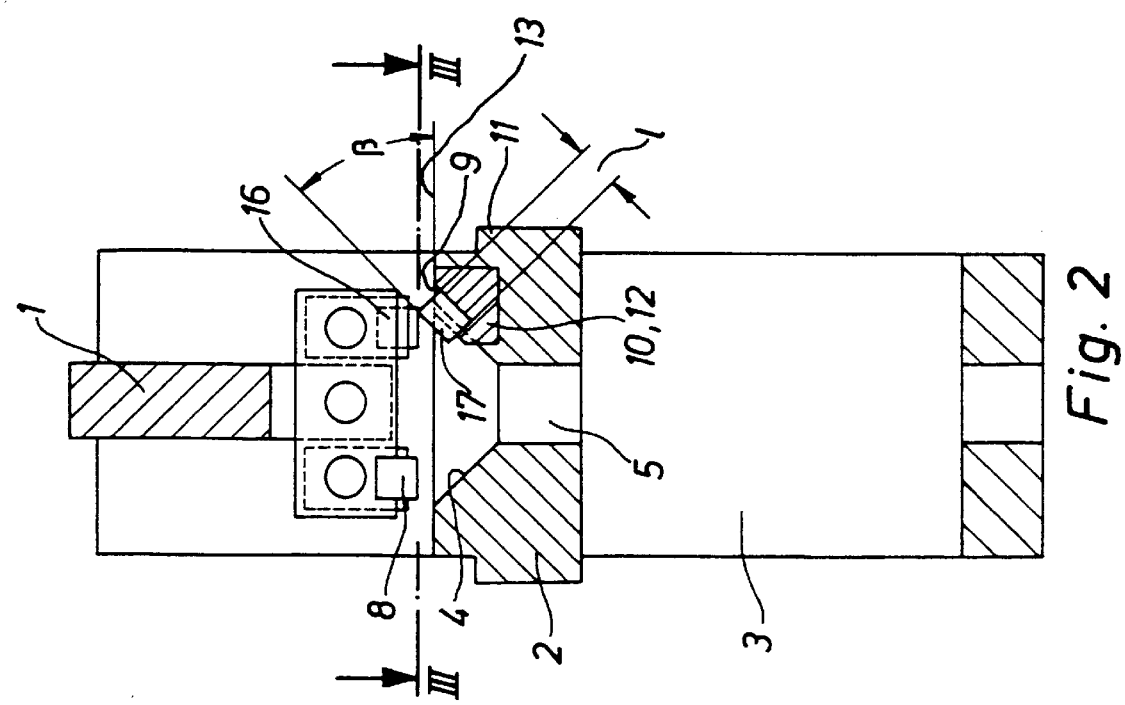

| Variant | Characteristics | | Remarks |
|---|---|---|---|
| Number | Roller Contact Pressure Length l (mm) | Opening Angle 2α (°) | |
| 1 | 8 | 40 | Standard—Starting Variant |
| 2 | 2,5 | 40 | Like 1, But Reduced Pressing Length |
| 3 | 2,5 | 60 | Like 2, But Larger Opening Angle |
| 4 | 2,5 | 30 | Like 2, But Smaller Opening Angle |

Fig. 5

METHOD AND ARRANGEMENT FOR MECHANICALLY TESTING THE VALVE DISK OF CERAMIC VALVES

BACKGROUND AND SUMMARY OF THE INVENTION

This application claims the priority of German application 198 47 210.2, filed in Germany on Oct. 13, 1998, the disclosure of which is expressly incorporated by reference herein.

The invention relates to a method for testing valve disks of ceramic charge cycle valves for internal-combustion engines as well as to an arrangement for carrying out the method.

During mechanical strain, ceramic materials fail at defective spots, which may be natural sintering defects as well as defects caused by processing, such as grinding cracks, or thermally induced cracks. Depending on the type of strain, surface defects or volume defects are decisive with respect to the failure.

For reasons of cost, inlet and outlet valves made of silicon nitride ($Si_3N_4$), during the manufacturing from the sintered blank by means of diamond wheels, must be ground at a high cutting speed and cutting capacity. This means that defects are produced in the surface and in the edge zone close to the surface. These may be cracks, shattered portions of material and deep chatter marks. The defects are only partially removed during the finishing grinding. As a rule, grinding cracks remain in the material. During the operation, the failure of ceramic inlet and outlet valves often takes place in the valve disk edge area. The targeted testing of the valve disk edge after the manufacturing of the valves is therefore a priority of quality assurance. It cannot be carried out by means of nondestructive testing methods or can be carried out only at very high expenditures.

From Japanese Patent Document JP 3-264,713 A, it is known to test ceramic valves by means of a tension test. For this purpose, the valve disk, on the one hand, and the valve stem, on the other hand, are clamped into corresponding receiving devices.

It is therefore an object of the invention to provide a testing method and/or an arrangement by means of which ceramic valves can be tested more easily; particularly the breaking action and the breaking origin can be observed more easily; and thus defects caused by processing can be determined with respect to their extent and effect by measuring the strength.

According to preferred embodiments of the invention, this object is achieved by a method for testing valve disks of ceramic charge cycle valves for internal-combustion engines, comprising selecting three stressing points within half the circumference of the valve disk, introducing a pressure by means of stressing devices into two of the stressing points provided on a valve seat side of the valve disk, and introducing a pressure by means of a stressing device into the third stressing point provided on a side of the valve disk facing away from the valve seat, wherein the stressing points are situated in a radially exterior area of the valve disk in the area of the valve seat, and wherein one of said stressing points is placed between the two other stressing points.

Thus, a valve disk is stressed with respect to bending along a portion of its edge area which is smaller than half the circumference such that the truncated-cone-shaped valve seat side of the valve disk is stressed under tension. In this case, a pressure is exercised by means of a stressing device particularly in the axial direction at a first stressing point of the valve disk on the side of the valve disk situated opposite the valve seat, and a counterpressure is exercised at two stressing points on the valve seat side. Viewed in the circumferential direction, the two stressing points of the valve seat side are situated on this side and on the opposite side of the stressing point provided on the side facing away from the valve seat. The three stressing points are situated within an area which corresponds to half the circumference of the valve disk.

The three stressing points may preferably be situated within a narrower area which corresponds to one sixth to one twelfth of the circumference.

In this manner, this area of the valve disk is locally stressed by bending, in which case the valve seat side is stressed under tension so that a failure of the valve disk is caused which is close to reality and can be reproduced.

Instead of cones or balls, which produce punctiform pressure points, cylindrical or truncated-cone-shaped rollers can be used as stressing devices, which introduce the load by way of a surface line into the valve disk. The stressing points will then be contact lines. These contact lines are preferably radially aligned on the side facing away from the valve seat.

The two contact lines on the valve seat side may extend mirror-symmetrically to one another with respect to an axial plane extending through the first contact line. However, a radial alignment of these contact lines is also contemplated.

On the diametrically opposite, circumferential side of the valve disk, stops are situated for the radial holding or fixing of the valve disk in relation to the stressing devices.

If the pressure points are designed correspondingly, the two contact lines on the valve seat side may be shorter than the width of the disk edge.

The method is implemented by means of an arrangement including a testing machine with a support for the valve disk and a pressure foot for exercising a pressure force onto the valve disk. In preferred embodiments of the invention, this bending test arrangement has a support and a pressure foot wherein, on the valve seat side of the valve disk, the support is equipped with two stressing rollers mirror-invertedly arranged with respect to an axial plane. A stop roller is situated on the side diametrically opposite the two stressing rollers.

Additional advantages, characteristics and details of the invention are contained in the claims as well as in the following description, in which a particularly preferred embodiment is described in detail with reference to the drawing. In this case, the characteristics illustrated in the drawing and indicated in the claims as well as in the description may in each case be essential to the invention individually or in any combination.

Other objects, advantages and novel features of the present invention will become apparent from the following detailed description of the invention when considered in conjunction with the accompanying drawings.

BRIEF DESCRIPTION OF THE DRAWINGS

FIG. 1 is a schematic lateral view of the pressure arrangement according to the invention;

FIG. 2 is a sectional view II—II of the arrangement according FIG. 1;

FIG. 5 is a table of parameter settings for the pressure arrangement.

DETAILED DESCRIPTION OF THE DRAWINGS

Figure 3:
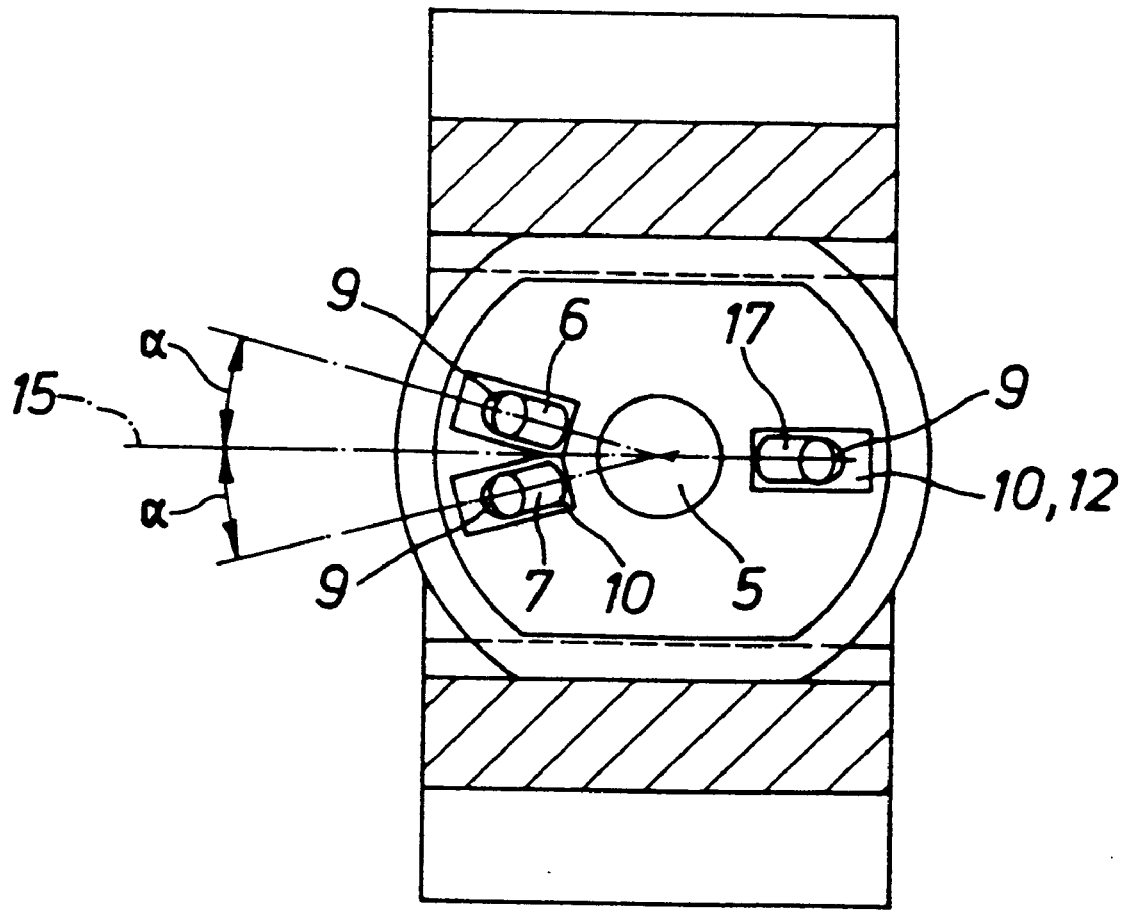
FIG. 3 is a sectional view III—III of the arrangement according to FIG. 2.

The pressure arrangement illustrated in FIGS. 1 to 3, which can be used in a commercially available universal testing machine, consists of a pressure foot 1 and of a support 2 which are arranged in a frame 3. The support 2 has a truncated-cone-shaped recess 4, which corresponds to a valve disk 19 (FIG. 4), and a cylindrical bore 5 corresponding to a valve stem 20, in order to receive the valve seat side 21 of the valve disk 19. The actual support 2 for the valve disk 19 consists of three rollers 6, 7 and 17, as illustrated in FIG. 3. The rollers 6, 7 and 17 themselves are disposed in semicylindrical recesses 9 of a carrier 10. Instead of designing the support 2 in one piece, it is advantageous to provide a support carrier 11 with recesses into which exchangeable inserts 12 can be placed. The inserts 12 are exchangeable so that corresponding inserts 12 for rollers 6, 7 and 17 can be used which have different diameters, at different radii, that is, with different distances from the valve stem 20, and with different angles of incidence $\beta$. The angle of incidence $\beta$ is the angle between the plane 13 of the valve disk 19 and the axis of the roller 6, 7 or 17.

FIG. 3 shows the rollers 6, 7 and 17 whose longitudinal axes in the radial direction with respect to the valve axis 14. The two rollers 6 and 7 are situated at an angle $2\times\alpha$, which is called an opening angle, of 30° with respect to one another. They are also situated symmetrically with respect to a vertical plane 15 which extends through the roller 17. The angle $\alpha$ between the rollers 6 and the plane 15, and between the roller 7 and the plane 15 therefore amounts to 15° respectively. This angle $\alpha$ can be adjusted in that different inserts 12 are used which receive the rollers 6 and 7 at different angles $\alpha$.

As illustrated in FIG. 2, the angle of incidence $\beta$ can be adjusted by inserts 12 with more or less inclined recesses 9. Angles of incidence $\beta$ between 25° and 65° are conceivable. FIG. 2 shows an embodiment with an angle of incidence $\beta$ of 45°.

The pressure foot 1 is equipped with two rollers 8 and 16, specifically the stressing roller 8 and a stop roller 16. These two rollers 8, 16 are radially aligned and are situated diametrically opposite one another. The pressure foot 1 is arranged above the support 2 in such a manner that, viewed in the axial direction, the stop roller 16 is situated above the stop roller 17 of the support 2. Viewed in the axial direction, the stressing roller 8 of the pressure foot 1 is situated in the center between the two stressing rollers 6 and 7 of the support 2. In the embodiment illustrated in the drawing, all stressing rollers 6 to 8 and stop rollers 16 and 17 are radially aligned.

However, the axes of the rollers 6 to 8, 16, 17 and therefore their surfaces lines can also be situated at an angle with respect to the respective radii. Instead of cylindrical rollers 6 to 8, 16, 17, truncated-cone-shaped rollers may also be used which are situated in correspondingly truncated-cone-shaped recesses 9 of the support 2.

In order to improve the reproducibility of the breaking action of the tested ceramic valves 18, on the one hand, in a mechanical analysis by computer, decisive parameters, such as the roller length 1 of the rollers 6 to 8, 16, 17 and the opening angle ($2\alpha$) of the rollers 6, 7 with respect to one another are tested and, on the other hand, the results of an FE (finite element) analysis are adjusted by real tests on the above-described bending test arrangement.

EXAMPLE 1

Mechanical Analysis on the Ceramic Valve

Figure 4:
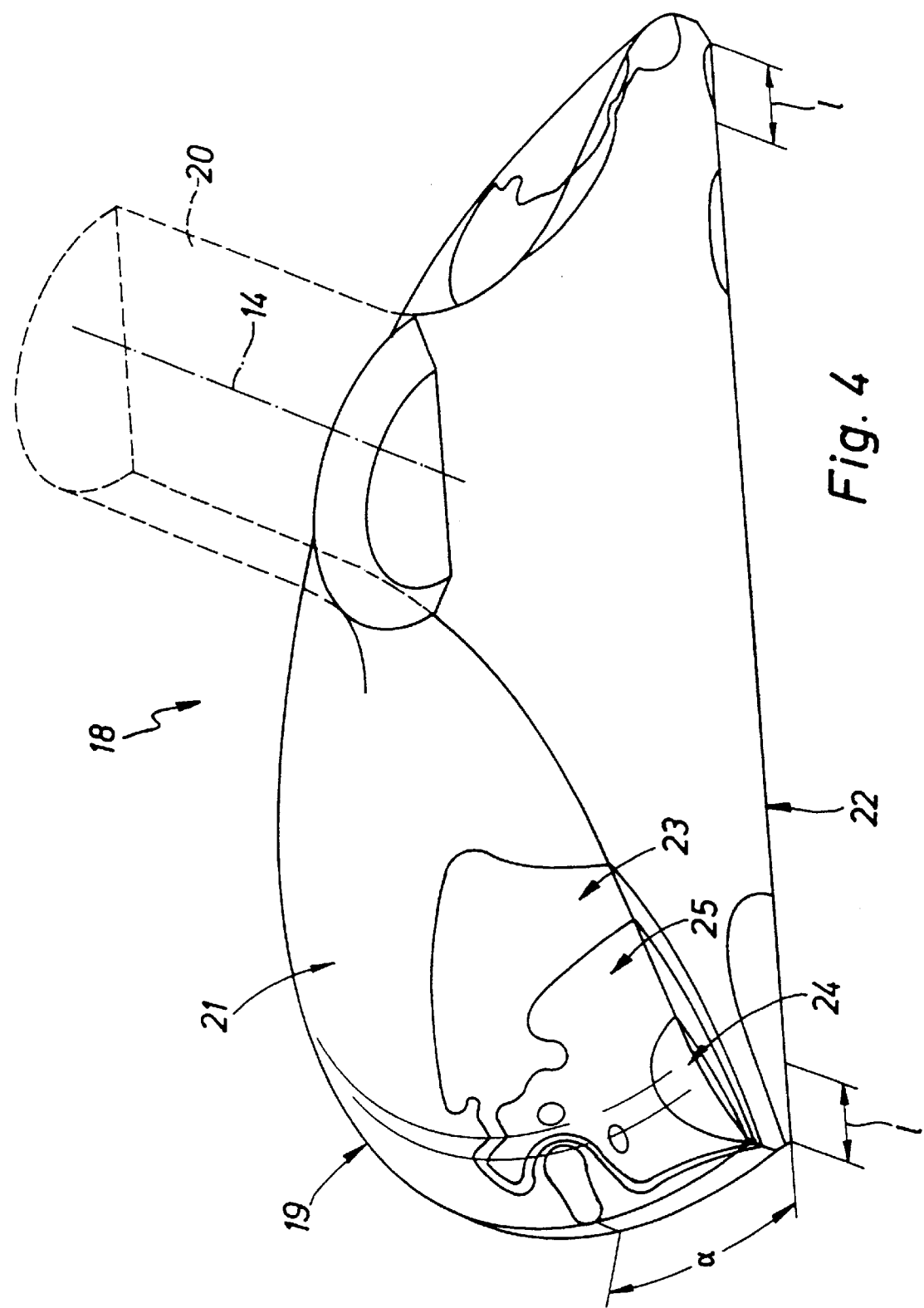
FIG. 4 is a view of an FE analysis of the maximal principal tension of a variant of the arrangement.

The FE analysis was carried out on an inlet valve with a diameter of 34 mm. The load was 9.9 kN; the E-module 300 GPa, and Poisson's number was 0.27. The contact length 1 of the rollers was set at 8 mm. During the linear-elastic analysis, 3D finite elements (FE) with a square projection were used. The computer model has 13332 degrees of freedom. For reasons of symmetry, only half the geometry is taken into account during the computation. FIG. 4 reflects the distribution of the largest principal tension in the MPa (N/mm$^2$), in the case of a contact pressure length 1 of 8 mm and an angle a of 20°. It is illustrated that large tensions in the edge area of the valve disk 19 as well as in the interior portion of the valve disk 19 occur in a zone 23 and in the proximity of the supporting rollers 16 and 17. Up to a distance of approximately 8 mm from the edge, in a zone 25, the tensile stresses exceed a value of 430 MPa. The maximal tensile stress is at 1,080 MPa in a zone 24 below the central stressing roller 8, and the breaking stress of 900 MPa is reached at a distance of approximately 4 mm from the edge. The area under tension comprises not only the valve disk edge but also areas which are away from the disk edge: This FE analysis results in a breaking action which can be reproduced.

The results of the tests on the bending test arrangement correspond to this FE analysis.

EXAMPLE 2

Mechanical Analysis in the Valve When the Load Introduction is Changed

The stressing and the material data correspond to Example 1. The contact pressure lengths 1 of the rollers 6 to 8, 16, 17 and the opening angle $2\alpha$ are changed. The parameter setting is summarized in FIG. 5.

The comparison of the FE analyses at the parameter settings 2, 3 and 4 of the table shows that, when the contact pressure length L is shortened from 8 mm to 2.5 mm, the valve disk edge is stressed more and in a more localized manner. The FE analysis also shows that an increase of the opening angle $2\alpha$ of the rollers 6 and 7 from 40° to 60° results in a higher tension level, and that the area which is considerably endangered by breakage extends farther into the interior of the disk. In contrast, a reduction of the opening angle $2\alpha$ from 40° to 30° causes a very high and narrowly limited stressing of the material at the disk edge.

An optimal load introduction is mathematically determined at the shortened roller contact pressure length 1 and a smaller opening angle $2\alpha$ for the rollers 6 and 7. In order to experimentally investigate the influence of a shortening of the contact pressure length 1 on the breakage action of the valve edge, obliquely ground contact pressure rollers having a diameter of 8 mm from a roller bearing were used. The contact pressure length 1 amounts to approximately 4 mm. The tests confirm the mathematical prediction. The breakage area is limited to the disk edge. The breaking load varies between 12 kN and 15 kN. The breaking surface comprises an area of approximately 10×15 mm$^2$.

These examples show that the mathematical detection of the mechanical action of ceramic valves 18 and the destructive three-point bending tests permit an optimizing of the load introduction in the valve disk edge. Because of the high local stressing, a reproducible controlled breaking action of the valve 18 is obtained. The tests show that, by means of the new testing arrangement, six tests per valve 18 can be carried out. The number of tested valves 18 can thereby be reduced to half the former number. This results in a number of testing possibilities, such as:

Multiple testing on one valve (approximately 6 tests per valve 18);

measuring of the influence of defined defects on the strength, such as cracks made in a defined manner by hardness denting, measuring the effects of pores on the stability;

optimizing of the grinding process by measuring the breaking strength on the component with technical surfaces;

measuring the fatigue and the endurance limit in the case of cyclical stress.

Finally, within the scope of the invention, the dimensions and the arrangement of the bending testing arrangement can be varied such that the method can be used universally for testing valves 18 with different dimensions.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. Method for testing valve disks of ceramic charge cycle valves for internal-combustion engines, comprising the steps of:

selecting three stressing points within half of a circumference of a valve disk, introducing a pressure by means of a first and a second stressing device into two of the stressing points provided on a valve seat side of the valve disk, and introducing a pressure by means of a third stressing device into a third stressing point provided on an opposite side of the valve disk, wherein the stressing points are situated in a radially exterior area of the valve disk in an area of the valve seat, and wherein the third of said stressing points is placed between the two other stressing points.

2. Method according to claim 1, wherein the valve seat side of the valve disk is stressed under tension.

3. Method according to claim 1, wherein by means of at least one of the stressing devices, a pressure directed in an axial direction of the valve is exercised on at least one of two sides of the valve disk.

4. Method according to claim 2, wherein, by means of at least one of the stressing devices, a pressure directed in an axial direction of the valve is exercised on at least one of two sides of the valve disk.

5. Method according to claim 1, wherein, by means of at least one of the stressing devices, a pressure directed in an orthogonal direction to a respective surface is exercised on at least one of two sides of the valve disk.

6. Method according to claim 1, wherein, by means of the stressing devices, a punctiform, linear or laminar stress is introduced into the valve disk.

7. Method according to claim 6, wherein, in case of a linear stressing, a stressing line of at least one stressing device is radially aligned.

8. Method according to claim 5, wherein, in case of a linear stressing, stressing lines of the two stressing devices applied to one side of the valve disk are mirror-invertedly arranged with respect to a plane containing an axis of a valve stem.

9. Method according to claim 1, wherein the valve disk is radially supported or fixed on a side situated approximately diametrically opposite the stressing points.

10. A device for testing valve disks of ceramic charge cycle valves for internal-combustion engines, said device comprising:

a support for a valve disk, and a pressure foot for exercising a pressure force onto the valve disk, wherein the support is constructed for receiving a valve seat side of the valve disk, wherein the support has a receiving device for two stressing devices which are applied within half a circumference to a valve seat side in a radially exterior area of the valve disk, in an area of the valve seat, and wherein, at the pressure foot on an opposite side of the valve disk, a third stressing device is provided which is situated between said two stressing devices and in the radially exterior area of the valve disk.

11. The device according to claim 10, wherein the stressing devices are stressing rollers, stressing cones or stressing balls.

12. The device according to claim 10, wherein the stressing devices are stressing rollers which are radially aligned with a valve stem axis of a valve being tested.

13. The device according to claim 10, wherein the stressing devices applied to the valve seat side of the valve disk are arranged mirror-invertedly with respect to a plane containing an axis of the valve stem.

14. The device according to claim 11, wherein the stressing devices are stressing rollers, and
wherein a length of the stressing rollers is between 2 mm to 10 mm.

15. The device according to claim 12, wherein the stressing devices are stressing rollers, and
wherein a length of the stressing rollers is between 2 mm to 10 mm.

16. The device according to claim 14, wherein the length of the stressing rollers is between 2.5 mm and 8 mm.

17. The device according to claim 14, wherein the length of the stressing rollers is between 4 mm and 6 mm.

18. The device according to claim 11, wherein the stressing devices are stressing rollers, and
wherein stressing lines of the stressing rollers are shorter than a width of an edge of the valve disk.

19. The device according to claim 18, wherein the stressing devices applied to the valve seat side of the valve disk are arranged mirror-invertedly with respect to a plane containing an axis of the valve stem.

20. The device according to claim 18, wherein the length of the stressing rollers is between 2 mm to 10 mm.

21. The device according to claim 11, wherein the stressing devices are stressing rollers, and
wherein said two of said stressing rollers resting against the valve seat side of the valve disk are arranged offset in a circumferential direction in each case by an angle α of ±15° to ±30° with respect to said other stressing roller resting on the opposite side of the valve disk.

22. The device according to claim 13, wherein the stressing devices are stressing rollers, and
wherein said two of said stressing rollers resting against the valve seat side of the valve disk are arranged to be offset in a circumferential direction in each case by an angle α of ±15° to ±30° with respect to said other stressing roller resting on the opposite side of the valve disk.

23. The device according to claim 14, wherein the two of said stressing rollers resting against the valve seat side of the valve disk are arranged to be offset in the circumferential direction in each case by an angle α of ±15° to ±30° with respect to the other stressing roller resting on the opposite side of the valve disk.

24. The device according to claim 22, wherein a length of the stressing rollers is between 2 mm to 10 mm.

25. The device according to claim 11, wherein the stressing devices are stressing rollers, and wherein an angle β between a plane of the valve disk and the axis of the stressing roller is between 25° and 65°.

26. The device according to claim 25, wherein said angle is 45°.

27. The device according to claim 25, wherein a length of the stressing rollers is between 2 mm to 10 mm.

28. The device according to claim 25, wherein stressing lines of the stressing rollers are shorter than the width of the edge of the valve disk.

29. The device according to claim 25, wherein said two of said stressing rollers resting against the valve seat side of the valve disk are arranged to be offset in a circumferential direction in each case by an angle α of ±15° to ±30° with respect to said other stressing roller resting on the opposite side of the valve disk.

30. The device according to claim 10, wherein the stressing devices provided in the receiving device are situated in recesses of an exchangeable insert.

31. The device according to claim 30, wherein the stressing devices are stressing rollers, stressing cones or stressing balls.

32. The device according to claim 10, wherein the pressure foot has a pressure roller and a stop roller which are radially aligned and are situated diametrically opposite one another.

33. The device according to claim 32, wherein, viewed in an axial direction, the stop roller of the pressure foot and a stop roller of the support are arranged above one another.

34. The device according to claim 10, wherein the stressing devices are stressing rollers, and wherein the stressing rollers have a diameter which corresponds to 5% to 15% of a diameter of the valve disk.

35. A method of testing valve disks of ceramic charge cycle valves for internal combustion engines in a universal testing machine having a frame supporting a pressure foot and a valve support for a valve being tested, said method comprising the steps of:

introducing pressure against a valve disk held in the machine between the pressure foot and the valve support to break the valve disk, and monitoring effects of said pressure on the valve disk, wherein said step of introducing pressure includes forcing first and second stressing devices against a valve seat side of the valve disk at respective first and second stressing locations and forcing a third stressing device against a side of the valve disk opposite said valve seat side and at a third stressing location disposed intermediate said first and second stressing locations, wherein the stressing locations are situated in a radially exterior area of the valve disk in an area of the valve seat.

36. A method according to claim 35, wherein said stressing locations are all situated within an area which corresponds to less than half a circumference of the valve disk.

37. A method according to claim 36, wherein said stressing locations are all situated within an area which is between one sixth to one-twelfth of the circumference of the valve disk.

38. A method according to claim 35, wherein said stressing devices are stressing rollers.

39. A method according to claim 37, wherein said stressing devices are stressing rollers.

40. A method according to claim 38, wherein said stressing rollers are radially aligned with respect to an axis of said valve disk.

41. A method according to claim 39, wherein said stressing rollers are radially aligned with respect to an axis of said valve disk.

42. A method according to claim 38, wherein said stressing rollers each has a length of between 2 mm and 10 mm.

43. A method according to claim 41, wherein said stressing rollers each has a length of between 2 mm and 10 mm.

44. A method according to claim 38, wherein the stressing devices are stressing rollers, and wherein the stressing rollers have a diameter which corresponds to 5% to 15% of a diameter of the valve disk.

* * * * *